United States Patent [19]
Lösel et al.

[11] Patent Number: 5,665,729
[45] Date of Patent: Sep. 9, 1997

[54] CEREBROPROJECTION METHOD

[75] Inventors: Walter Lösel, Gau-Algesheim; Otto Roos, Schwabenheim; Dietrich Arndts, Appenheim; Franz Josef Kuhn, Gau-Algeshiem; Ilse Strelle, Stromberg, all of Germany

[73] Assignee: Boehringer Ingelheim KG, Ingelheim am Rhein, Germany

[21] Appl. No.: 456,357

[22] Filed: Jun. 1, 1995

Related U.S. Application Data

[62] Division of Ser. No. 238,298, May 5, 1994, abandoned, which is a continuation of Ser. No. 36,299, Mar. 24, 1993, abandoned, which is a continuation of Ser. No. 812,321, Dec. 23, 1991, abandoned, which is a continuation of Ser. No. 809,610, Dec. 17, 1991, abandoned.

[30] Foreign Application Priority Data

Dec. 22, 1990 [DE] Germany .................... 40 41 482.5

[51] Int. Cl.$^6$ .................... A61K 31/475; A61K 31/47; A61K 31/435
[52] U.S. Cl. .................... 514/292; 514/300; 514/301; 514/307
[58] Field of Search .................... 514/307, 292, 514/300, 301

[56] References Cited

U.S. PATENT DOCUMENTS 4,322,418  3/1982  Lösel et al. .................... 546/90

FOREIGN PATENT DOCUMENTS

| 598558 | 1/1988 | Australia . |
|---|---|---|
| 0251194 | 1/1988 | European Pat. Off. . |
| 3621413 | 1/1988 | Germany . |
| 3827727 | 2/1990 | Germany . |

OTHER PUBLICATIONS

Stroke A Journal of Cerebral Circulation, vol. 17, No. 4, Jul.–Aug. 1986—"*The Effect of the Calcium Antagonist Nimodipine on the Gerbil Model of Experimental Cerebral Ischemia*"—A. Fujisawa, et al., pp. 748–752.

*Primary Examiner*—Bernard Dentz
*Attorney, Agent, or Firm*—R. P. Raymond; M-E. M. Devlin; A. R. Stempel

[57] ABSTRACT

The invention relates to the use of carbocyclically and heterocyclically fused dihydropyridines as cerebroprotective agents, as agents for treating chronic inflammatory processes and as agents for inhibiting blood clotting, and also relates to new compounds of formula Ie

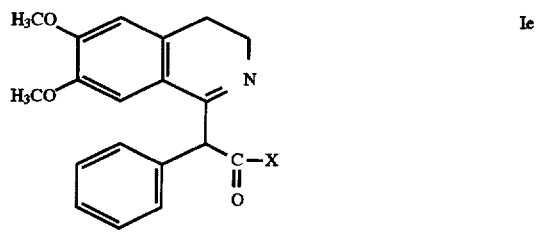

9 Claims, No Drawings

CEREBROPROJECTION METHOD

This is a division of application Ser. No. 08/238,298, filed May 5, 1994 now abandoned, which is a continuation of application Ser. No. 08/036,299, filed Mar. 24, 1993 (abandoned), which is a continuation of application Ser. No. 07/812,321, filed Dec. 23, 1991 (abandoned), which is a continuation of application Ser. No. 07/809,610, filed Dec. 17, 1991 (abandoned).

Dihydroisoquinolines of general formula are known from EP-A 37 934. The compounds mentioned therein have a cardiotonic effect and have the effect of increasing contractility and influencing blood pressure. They have been proposed for improving the blood flow through the tissues and improving the oxygen supply to the tissues. These possible applications are based on the vascular activity of the compounds. EP-A 251 194 describes how carbocyclically and heterocyclically fused dihydropyridines have a cardioprotective effect and constitute a totally new type of Ca-antagonistic compounds.

The present invention relates to the use of the compounds known from the above-mentioned EP-A 251 194 as cerebroprotective agents, particularly for treating patients who have suffered a stroke or are at risk of suffering a stroke. The invention further relates to the use of these compounds for treating chronic inflammatory processes (e.g. bronchial asthma, arthritis) and for inhibiting blood coagulation or blood platelet aggregation. The invention further relates to a group of new fused dihydropyridines, namely new 3,4-dihydroisoqinoline derivatives of general formula Ie as defined hereinafter.

The invention thus relates to the use of carbocyclically and heterocyclically fused dihydropyridines of the formula

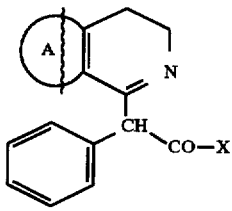

I including the tautomeric forms thereof of formula II, this term representing the cis- and trans-forms II' and II" together:

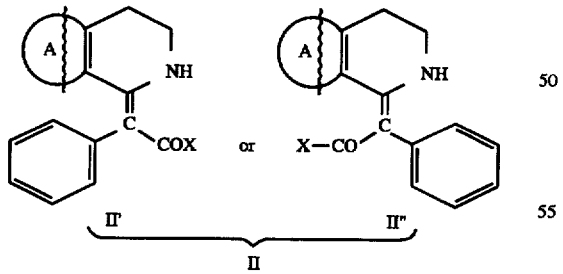

II wherein X represents $OR_1$; $NHR_2$; $NR_3R_4$
and $R_1$ represents hydrogen, $C_{1-4}$-alkyl, $C_{1-4}$-alkoxyalkyl $R_2$ represents hydrogen; $C_{3-6}$-alkenyl, $C_{3-6}$-alkynyl; $C_{3-6}$-cycloalkyl; $C_{3-6}$-cycloalkenyl; straight-chained or branched $C_{1-6}$-alkyl which may if desired be mono- or polysubstituted with the substituents of groups a) to c) listed below, which may be identical or different:

a) halogen; cyano; hydroxy; mercapto; $C_{1-4}$-alkoxy; $C_{1-4}$-alkylthio; amino; mono-$C_{1-4}$-alkylamino; di-$C_{1-4}$-alkylamino (wherein the alkyl radical may be identical or different), phenoxy (wherein the phenyl group may be substituted as in b) below)

b) phenyl; optionally mono- or polysubstituted, by identical or different substituents, by the groups halogen, trifluoromethyl $C_{1-4}$-alkoxy, hydroxy, mercapto, $C_{1-4}$-alkylthio, $C_{1-4}$-alkyl, amino, mono-$C_{1-4}$-alkylamino, di-$C_{1-4}$-alkylamino (wherein the alkyl groups may be identical or different), $C_{2-3}$-acylamino, $C_{2-3}$-acyloxy and the group —O—$(CH_2)_n$—O vicinally by bound to the phenyl system (wherein n=1 or 2)

c) a 5- or 6-membered saturated or wholly or partially unsaturated monocyclic heterocyclic group having up to 3 heteroatoms selected from the group N, O, S; and as a bicyclic heterocycle indole (whilst the above-mentioned heterocycles may be mono- or polysubstituted by $C_{1-4}$-alkyl), $C_{3-6}$-cycloalkyl; $C_5$-or $C_6$-cycloalkenyl; $C_{2-3}$-acyl; $C_{1-4}$-alkylsulphonyl; or phenyl (which may in turn be substituted up to three times as described in b));

or $R_2$ represents phenyl, which may be substitued as described in b) above;

$R_3$ and $R_4$ independently of each other represent $C_{1-4}$-alkyl, which may if desired be phenyl-substituted, whilst the phenyl substituent may in turn be substituted as under b) hereinbefore;

or $R_3$ and $R_4$ together with the nitrogen atom to which they are bound represent a wholly or partially saturated heterocyclic 5- or 6-membered ring (which may also contain up to 2 further heteroatoms from the group N, O, S), whilst the heterocyclic group thus obtained may be substituted by $C_{1-4}$-alkyl, hydroxy or $(CH_2)_p$-$R_5$ (where p=0 or 1)

and $R_5$ represents a phenyl radical which is optionally substituted as under b) hereinbefore;

A represents the fused ring systems

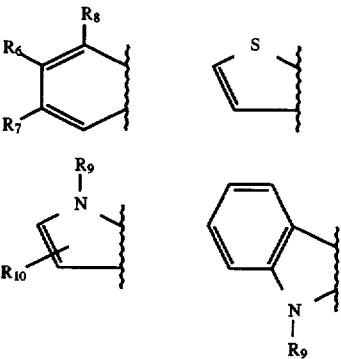

wherein $R_8$ represents hydrogen; $C_{1-4}$-alkyl or $C_{1-4}$-alkoxy $R_6$ and $R_7$ which may be identical or different represent hydrogen; hydroxy; $C_{1-4}$-alkyl; $C_{1-4}$-alkoxy; amino; methanesulphonylamino or $R_6$ and $R_7$ together represent —O—$(CH_2)_n$—O—(where n=1 or 2)

$R_9$ represents hydrogen; $C_{1-4}$-alkyl $R_{10}$ represents hydrogen or 2-phenyl-2-ethoxycarbonyl-acetyl and the salts thereof with physiologically acceptable acids, bases or complex-forming agents for cerebral protection for treating chronic inflammatory processes and for inhibiting blood coagulation or blood platelet aggregation.

Within the general formula I are included the new 3,4-dihydroisoquinoline derivatives of general formula Ie

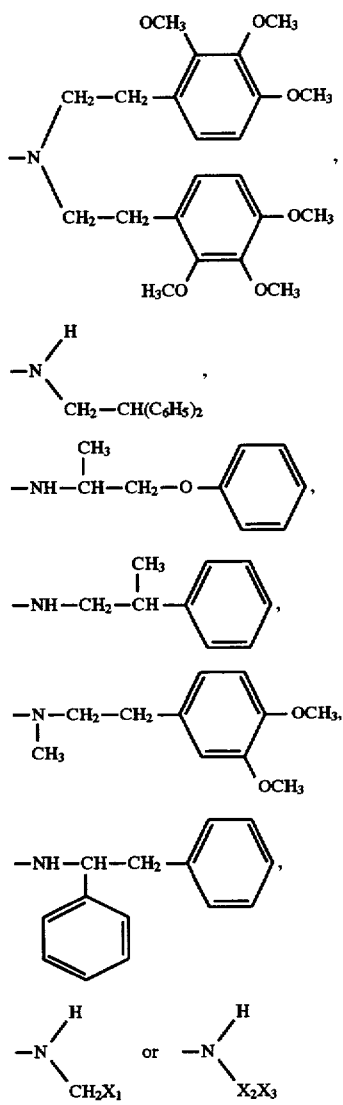

wherein X represents a group $X_1$ represents a phenyl group, mono- or di-substituted by a trifluoromethyl or ethoxy group, a phenyl group or a 2-methoxyphenyl group substituted by a fluorine atom and a methoxy group;

$X_2$ represents a group —$CH_2$—$CH_2$— or $CH_2$—CH($CH_3$); and $X_3$ represents a 2,3,4-trimethoxyphenyl, 2,3-dimethoxyphenyl, 2,6-dimethoxyphenyl or 3,6-dimethoxyphenyl group, mono- or di-substituted by a trifluoromethyl or ethoxy group or a phenyl group substituted by a methoxy group and a fluorine atom;

and their pharmaceutically acceptable salts.

These new compounds are also suitable for the uses described above.

Preferred are compounds of general formula Ie wherein X represents a group

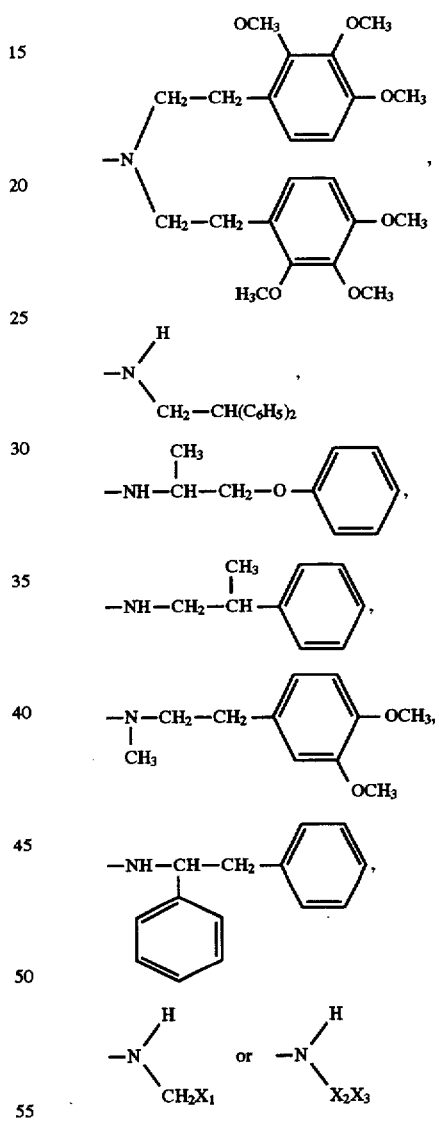

in which $X_1$ represents a 2-methoxyphenyl group which may optionally be additionally substituted by fluorine atoms;

$X_2$ represents a —$CH_2CH_2$— group; and $X_3$ represents a 2,3,4-trimethoxyphenyl, 2,3-dimethoxyphenyl, 2,6-dimethoxyphenyl, 3,6-dimethoxyphenyl, a 2- or 3-thienyl group, a phenyl group substituted by a trifluoromethyl or ethoxy group or a phenyl group substituted by a methoxy group and a fluorine atom.

It is preferred to use carbocyclically and heterocyclically fused dihydropyridines of formula

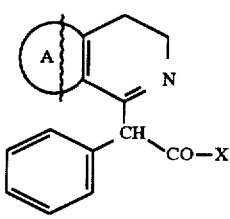

I and the tautomeric forms thereof of formula

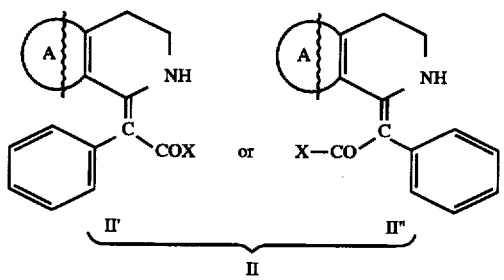

wherein X represents $OR_1$ $NHR_2$; $NR_3R_4$ $R_1$ represents methyl or ethyl $R_2$ represents hydrogen; straight-chained or branched unsubstituted $C_{1-5}$-alkyl; allyl; propargyl; $C_{3-6}$-cycloalkyl; 3-chlorophenyl; 2-methyl-3-chlorophenyl; or $C_{1-3}$-alkyl, which is mono-substituted with one of the substituents of groups d) to f) listed hereinafter;

d) cyano, hydroxy, methoxy, dimethylamino
  e) phenyl, 3,4-methylenedioxyphenyl, mono-, di- or trimethoxy substituted phenyl, 3-methoxy-4-hydroxyphenyl, 3-hydroxy-4-methoxyphenyl,
  f) morpholino, pyridin-2-yl, indol-3-yl, furan-2-yl, thiphen-2-yl, pyridin-3-yl, pyridin-4-yl $R_3$ and $R_4$ independently of each other represent methyl; ethyl; 3-cyanopropyl; benzyl; or 3,4,5-trimethoxyphenethyl or $R_3$ and $R_4$ together with the nitrogen atom to which they are bound represent morpholine; thiomorpholine; pyrrolidine; piperazine; 4-methylpiperazine; 4-benzylpiperazine; or 4-(2-methoxyphenyl)piperazine;

and

A represents the fused ring systems

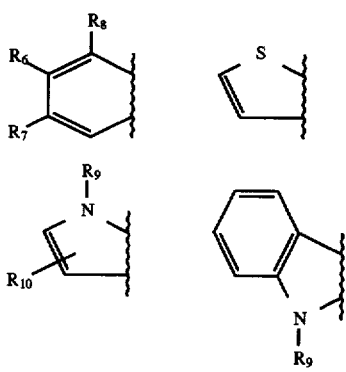

wherein $R_8$ represents hydrogen or methoxy $R_6$ represents methoxy; hydroxy; hydrogen; amino; or methanesulphonylamino $R_7$ represents hydrogen; methoxy; or hydroxy $R_9$ represents methyl $R_{10}$ represents 2-phenyl-2-ethoxycarbonylacetyl; or hydrogen and the salts thereof with physiologically acceptable acids.

The invention thus relates to dihydroisoquinolines of the formula

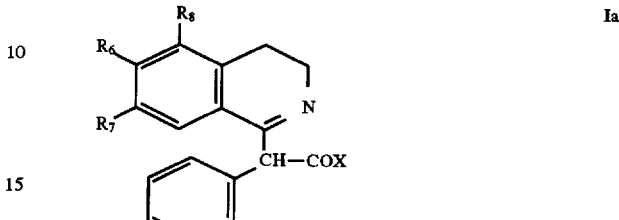

Ia dihydro-thieno[3,2-c]pyridines of the formula

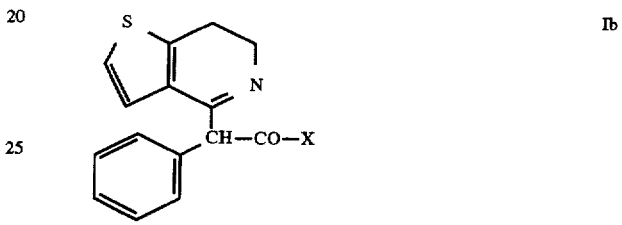

Ib dihydro-pyrrolo[3,2-c]pyridines of formula

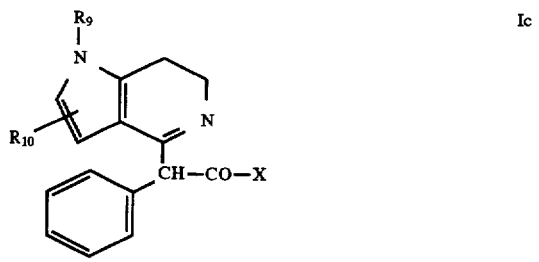

Ic and dihydro-pyrido[3,4-b]indoles of the formula

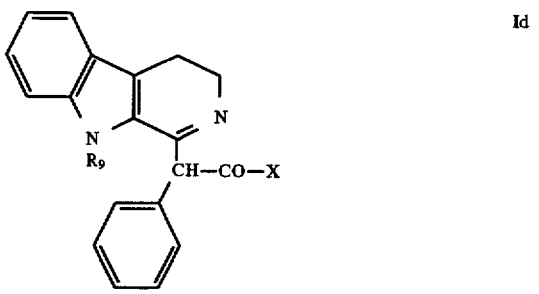

Id and the tautomeric forms thereof IIa', IIb', IIc' and IId' and the forms IIa", IIb", IIc" and IId" which are E/Z-isomeric thereto.

The compounds of formulae Ia to Id are chiral. The invention also includes the two R- and S-enantiomeric forms of the compounds of formula I wherein the meanings of the groups X, $R_6$, $R_7$, $R_8$, $R_9$ and $R_{10}$ are defined as hereinbefore.

The substances listed in Tables 1 to 12 hereinafter preferably occur in the tautomeric form I or II. In Table 12 the new compounds of general formula Ie are listed.

The preferred tautomeric form is designated I or II in the "structure" column.

The following compounds of formula I in tautomeric form I or II are listed by name.

TABLE 1

Structural type:

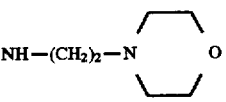

| No. | X | Structure |
|---|---|---|
| 1. | OCH$_3$ | II |
| 2. | OC$_2$H$_5$ | II |
| 3. | NHCH$_3$ | I |
| 4. | NHC$_2$H$_5$ | I |
| 5. | NH—(CH$_2$)$_2$—CH$_3$ | I |
| 6. | NH—(CH$_2$)$_3$—CH$_3$ | I |
| 7. | NH—(CH$_2$)$_4$—CH$_3$ | I |
| 8. | NH—CH(CH$_3$)$_2$ | I |
| 9. | NH—CH$_2$—CH(CH$_3$)$_2$ | I |
| 10. | NH—(CH$_2$)$_2$—CH(CH$_3$)$_2$ | I |
| 11. | NH—C(CH$_3$)$_3$ | I |
| 12. | NH—CH(CH$_3$)—C$_2$H$_5$ | I |
| 13. | NH—CH$_2$—CH=CH$_2$ | I |
| 14. | NH—CH$_2$≡CH | I |
| 15. | NH—(CH$_2$)$_2$—OH | II |
| 16. | NH—CH$_2$—CH(OH)—CH$_3$ | I |
| 17. | NH—(CH$_2$)$_2$—OCH$_3$ | II |
| 18. | NH—(CH$_2$)$_3$—OCH$_3$ | II |
| 19. | NH—(CH$_2$)$_2$—N(CH$_3$)$_2$ | I |
| 20. | NH—(CH$_2$)$_3$—N(CH$_3$)$_2$ | II |
| 21. | 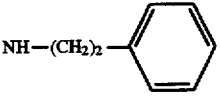 | II |
| 22. | 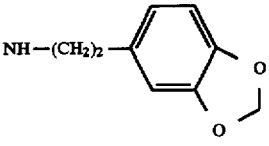 | I |
| 23. | 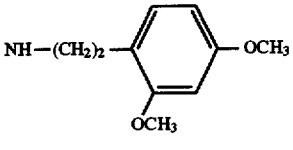 | I |
| 24. | 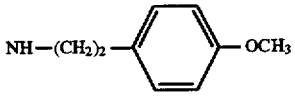 | I |
| 25. | 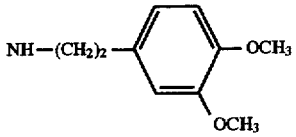 | I |
| 26. | 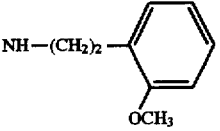 | II |

TABLE 1-continued

Structural type:

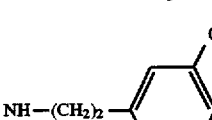

| No. | X | Structure |
|---|---|---|
| 27. | 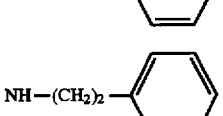 | II |
| 28. | 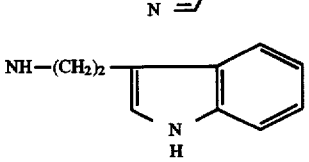 | I |
| 29. | 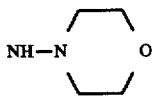 | I |
| 30. | 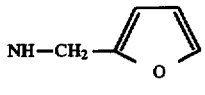 | II |
| 31. | 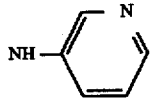 | I |
| 32. |  | II |
| 33. | 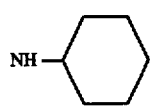 | I |
| 34. | NH—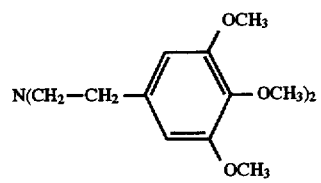 | I |
| 35. | NH—cyclohexyl | II |
| 36. | N(CH$_3$)$_2$ | I |
| 37. | N(C$_2$H$_5$)$_2$ | I |
| 38. | N(CH$_2$—CH$_2$—aryl(OCH$_3$)$_3$) | I |

TABLE 1-continued

Structural type:

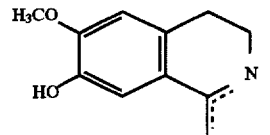

| No. | X | Structure |
|---|---|---|
| 38a. | N(CH₂—CH₂)₂ —[phenyl with OCH₃, OCH₃, OCH₃] | I |
| 39. | [morpholine] | I |
| 40. | [thiomorpholine] | I |
| 41. | [pyrrolidine] | I, II |
| 42. | [piperazine-N—CH₂—phenyl] | II |
| 43. | [N-methylpiperazine] | I |
| 44. | [piperazine-N—(2-methoxyphenyl)] | I |

TABLE 2

Structural type:

| No. | X | Structure |
|---|---|---|
| 45. | OC₂H₅ | II |
| 46. | NH—(CH₂)₂—[methylenedioxyphenyl] | II |
| 47. | NH—(CH₂)₂—[indole] | II |
| 48. | NH—(CH₂)₂—N[morpholine] | II |
| 49. | [morpholine] | II |
| 50. | [pyrrolidine] | I |

TABLE 3

Structural type:

[H₃CO, HO-substituted dihydroisoquinoline with Ph, C-X, O]

| No. | X | Structure |
|---|---|---|
| 51. | O₂H₅ | I |
| 52. | NH—(CH₂)₃—CH₃ | II |
| 53. | NH—(CH₂)₄—CH₃ | I |
| 54. | NH—CH(CH₃)₂ | I |
| 55. | NH—CH₂—CH(CH₃)₂ | I |
| 56. | NH—CH₂—CH=CH₂ | I |
| 57. | NH—(CH₂)₂—[phenyl] | I |

TABLE 3-continued

Structural type:

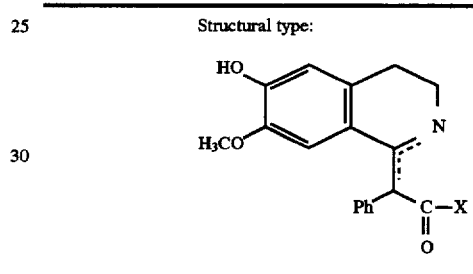

| No. | X | Structure |
|---|---|---|
| 58. | NH—(CH₂)₂—[2,5-dimethoxyphenyl with OCH₃ groups] | I |
| 59. | NH—(CH₂)₂—[phenyl with OCH₃ and OH] | I |
| 60. | NH—(CH₂)₂—[2-pyridyl] | I |
| 61. | NH—(CH₂)₂—N[morpholine]O | I |
| 62. | NH—[3-chlorophenyl] | I |
| 63. | NH—[2-methyl-3-chlorophenyl] | I |
| 64. | NH—[2-pyridyl] | I |
| 65. | NH—[3-pyridyl] | I |
| 66. | [piperazine]—[2-methoxyphenyl] | I |
| 67. | [morpholine] | I |

TABLE 3-continued

Structural type:

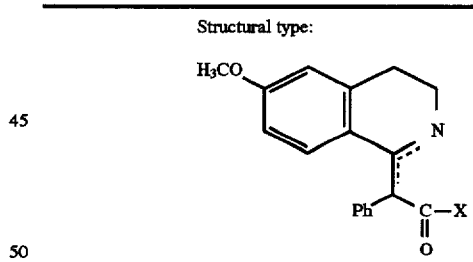

| No. | X | Structure |
|---|---|---|
| 68. | N(CH₂—CH₂—CN)(CH₂—phenyl) | I |

TABLE 4

Structural type:

[isoquinoline structure with HO, H₃CO, Ph, C(=O)—X]

| No. | X | Structure |
|---|---|---|
| 69. | N(C₂H₅)₂ | I |

TABLE 5

Structural type:

[isoquinoline structure with H₃CO, Ph, C(=O)—X]

| No. | X | Structure |
|---|---|---|
| 70. | NHCH₃ | I |
| 71. | NHC₂H₅ | I |
| 72. | NH—CH₂—[phenyl] | I |
| 73. | NH(CH₂)₂—[3-methoxyphenyl] | I |
| 74. | N(CH₃)C₂H₅ | I |

TABLE 6

Structural type:

[Structure: 3,4,5-trimethoxyphenyl dihydroisoquinoline with =C(Ph)COX substituent]

| No. | X | Structure |
|---|---|---|
| 75. | NH—CH₂—C₆H₅ (benzyl) | I |
| 76. | NH—(CH₂)₂—(2,3,4-trimethoxyphenyl) | I |
| 77. | N(CH₃)C₂H₅ | I |
| 78. | NH—(4-pyridyl) | II |
| 79. | N-methylpiperazinyl | I |

TABLE 7

Structural type:

[Structure: 6-(methanesulfonylamino)-dihydroisoquinoline with =C(Ph)COX substituent]

| No. | X | Structure |
|---|---|---|
| 80. | OC₂H₅ | II |

TABLE 8

Structural type:

[Structure: 6-amino-7-methoxy-dihydroisoquinoline with =C(Ph)COX substituent]

| No. | X | Structure |
|---|---|---|
| 81. | OC₂H₅ | II |

TABLE 9

Structural type:

[Structure: tetrahydro-β-carboline with =C(Ph)COX substituent]

| No. | X | Structure |
|---|---|---|
| 82. | OC₂H₅ | I, II |
| 83. | NH—(CH₂)₂—(3,4-dimethoxyphenyl) | II |
| 84. | NH—(CH₂)₂—(3,4-methylenedioxyphenyl) | II |
| 85. | NH—(CH₂)₂—(indol-3-yl) | I, II |
| 86. | morpholinyl | I |
| 87. | NH—CH₂—CH(CH₃)₂ | II |
| 88. | NH—(CH₂)₃—N(CH₃)₂ | II |
| 89. | NH—(CH₂)₂—morpholinyl | II |

TABLE 10
Structural type:
No. | X | Structure
--- | --- | ---
90. | OC$_2$H$_5$ | 
91. | NH—(CH$_2$)$_2$—[thiophene] | II
TABLE 11
Structural type:
No. | X | Structure
--- | --- | ---
92. | OC$_2$H$_5$ | II
TABLE 12
Structural type: I, II', II''
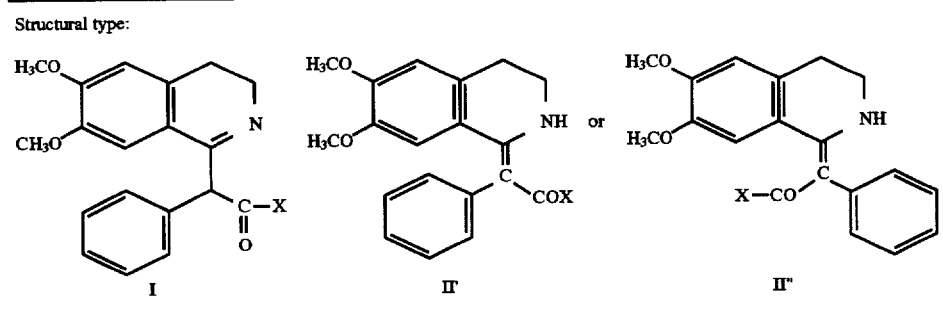
II
| Compound | X | Structure | M. pt (°C.) |
| --- | --- | --- | --- |
| A | —N(CH$_2$—CH$_2$—[3,4,5-(OCH$_3$)$_3$-C$_6$H$_2$])$_2$ · HCl | I | 56–64 |
| B | —N(H)(CH$_2$—CH$_2$—[2,3,4-(OCH$_3$)$_3$-C$_6$H$_2$]) · HCl | I | 176–184 |
| C | —N(H)(CH$_2$—CH(C$_6$H$_5$)$_2$) | I | 166–168 |

TABLE 12-continued
Structural type:
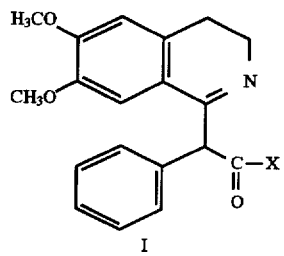
I
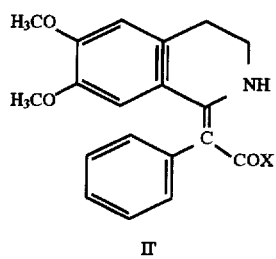
II'
or
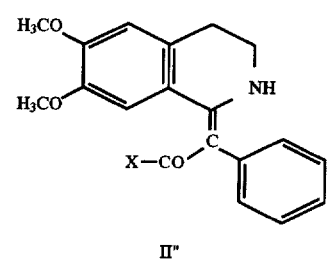
II"
II
| Compound | X | Structure | M. pt (°C.) |
|---|---|---|---|
| D | —NH—CH₂—CH₂-(thiophene) | II | 102–104 |
| E | —NH—CH₂—CH₂-(3-CF₃-phenyl) | I | 187 |
| F | —NH—CH₂-(2-F, 3-OCH₃-phenyl) | I | 94–96 |
| G | —NH—CH₂—CH₂-(2,3-dimethoxyphenyl) | II | 139–142 |
| H | —NH—CH(CH₃)—CH₂—O-phenyl | II | 133–135 |
| J | —NH—CH₂-(2-OCH₃-phenyl) | II | 143–145 |
| K | —NH—CH₂—CH₂-(2-OC₂H₅-phenyl) | II | 96–99 |
| L | —NH—CH₂—CH₂-(2,6-dimethoxyphenyl) | II | 118–120 |

TABLE 12-continued

Structural type:

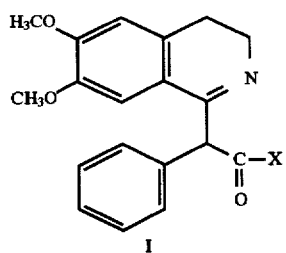 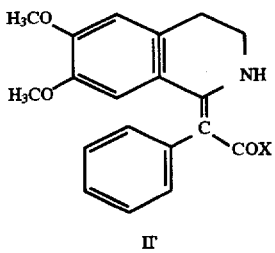 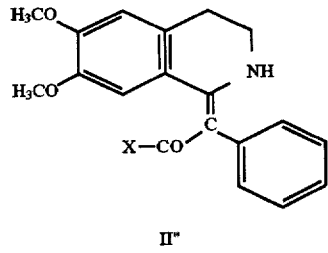

| Compound | X | Structure | M. pt (°C.) |
|---|---|---|---|
| M | 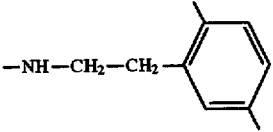 —NH—CH₂—CH₂—(3-OCH₃, 4-H₃CO-phenyl) | II | 122–114 |
| N | —NH—CH₂—CH(CH₃)—phenyl | II | 95–99 |
| O | —NH—CH₂—CH₂—(thiophene) | I | 114–116 |
| P | —N(CH₃)—CH₂—CH₂—(OCH₃, OCH₃-phenyl) | I | 66–73 |
| Q | —NH—CH(phenyl)—CH₂—phenyl | II | 205–209 |

In the definitions used in the text the radicals and groups may be identical or different, i.e. if one of the above-mentioned substituents occurs several times in a particular molecule, the meaning can be selected freely within the scope of the definitions provided.

The term alkyl means $C_{1-6}$-alkyl and $C_{1-4}$-alkyl radicals which may be substituted or, as alkyl radicals, are part of a functional group such as alkoxy or alkylthio. The alkyl radicals include methyl, ethyl, n-propyl, isopropyl, n-butyl, sec.-butyl, isobutyl and tert.-butyl radicals as well as the various isomeric pentyl and hexyl radicals, such as e.g. isopentyl, neopentyl, n-pentyl and n-hexyl radicals.

The above definition thus also applies even when the alkyl radical itself is substituted and/or is itself part of an alkoxyalkyl, alkoxycarbonyl, alkoxy, alkylthio, alkylsulphonyl, monoalkylamino, alkylmethyl, alkylthiomethyl or dialkylamino group or the alkyl radical, as a substituent, is bound to an aromatic heterocyclic or carbocyclic system.

The halogens are fluorine, chlorine, bromine and iodine, preferably fluorine, chlorine and bromine and, to a lesser extent, iodine.

$C_{3-6}$-cycloalkyl indicates cyclopropane, cyclobutane, cyclopentane and cyclohexane.

$C_{5-6}$-cycloalkenes denote e.g. cyclopentene, cyclohexene and cyclohexadiene.

The $C_2$- and $C_3$-acyl radicals denote acetyl and propionyl radicals.

$C_{3-6}$-alkynes are the isomeric hexynes, pentynes, butynes and propynes, preferably propargyl.

The $C_{3-6}$-alkenes are the isomeric hexenes, pentenes, butenes and propenes, preferably allyl.

Examples of unsaturated heterocyclic groups include, inter alia:

furan, pyran, pyrrole, pyrazole, imidazole, pyridine, pyrazine, pyrimidine, pyridazine, thiophene, thiazole, oxazole, 1,2,4-triazole, 1,2,3-triazole, 1,2,4-triazine, 1,3,5-triazine, indole.

Examples of 5- or 6-membered, wholly or partially saturated monocyclic heterocycles include, inter alia:

imidazolidine, pyrazolidine, pyrrolidine, piperidine, piperazine, morpholine, thiomorpholine, tetrahydrofuran, tetrahydrothiophene, 1,4-dioxine, imidazoline, pyrazoline, pyrroline, etc.

The compounds of formula I or II are bases and can be converted in the usual way with inorganic or organic acids and salts and complex-forming agents into any desired physiologically acceptable adducts (salts).

Acids suitable for salt formation include for example hydrochloric, hydrobromic, hydriodic, hydrofluoric, sulphuric, phosphoric, nitric, acetic, propionic, butyric, caproic, valeric, oxalic, malonic, succinic, maleic, fumaric, lactic, tartaric, citric, malic, benzoic, p-hydroxybenzoic, phthalic, cinnamic, salicylic, ascorbic, methanesulphonic acid and the like.

The majority of the compounds of general formula I and the methods of preparation thereof are known from EP-A 37 934 and EP-A 251 194 referred to above. These publications do not mention the compounds of formula Ie.

As already mentioned hereinbefore, the subject of the present invention is the use of the compounds known from the above-mentioned EP-A 251 194 and particularly the new compound of Example 38A) as a cerebroprotective agent. The compounds are valuable in the treatment of degenerative and necrotic diseases of the brain. It is also possible to provide preventative treatment for patients who are at risk from such diseases. As is shown by the experiments described hereinafter, the effect of the compounds is not based on an improvement in the blood flow through the tissues. The compounds are therefore suitable for a new kind of treatment of epilepsy and Alzheimer's disease and particularly for treating patients who have suffered a stroke or are at risk of suffering a stroke. Moreover, as mentioned earlier, the compounds are suitable for treating chronic inflammatory processes and for inhibiting blood clotting.

The following test results show the surprising efficacy of the compounds. The tests were carried out particularly on Compound A (Example 38A)

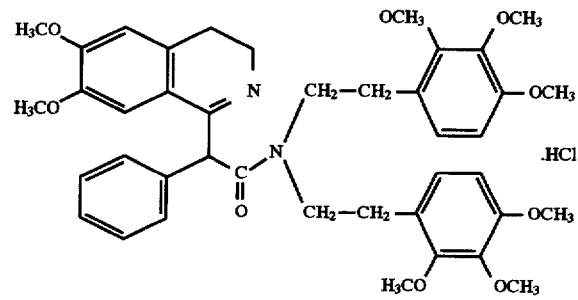

as a representative example of the compounds of general formula I.

Ischaemia tolerance in the gerbil: (e.g. Suzuki, R. et al., Acta Neuropath (Berl.) 1983, 60:207–216, 217–222; Yoshidomi, M. et al., J. Neurochem. 1989, 53:1589–1594) Ischaemia caused by occlusion of the carotid artery for 10 minutes under ether anaesthesia. Compound A was administered in doses of 1 and 10 mg/kg s.c. 4× within 24 hours, beginning 2 hours after the reopening of the arteries.

72 hours after the occlusion of the arteries the animals were killed and the brains were dissected for histological examination. As evidence of ischaemic damage or a reduction thereof, the damage to the cells in the vicinity of the $CA_1$-region of the hippocampus in a defined section of the histological preparation was evaluated. The test was carried out on groups of 5 animals.

In the group in which the animals were not given a test compound, all the animals showed significant damage to the $CA_1$-region examined. By contrast, when Compound A was administered, there was a clear dosage-dependent protection against the damage of hypoxia. When 1 mg/kg of Compound A was administered, only 2 out of 5 animals had any damage to the $CA_1$-region. When 10 mg/kg of Compound A were administered, none of the 5 animals showed any damage.

These results indicate that the compounds of general formula I can be used for the curative treatment of neurological damage, e.g. as caused by strokes.

The results of this trial also show that the compounds break through the blood-brain barrier, which is a major feature of the invention.

The following tests on isolated cell cultures show the mechanism of activity of the test compounds. From these test results (as from the results of tests on gerbils) it can be concluded that the compounds of general formula I can be used for the treatments mentioned in this patent application.

In isolated cell cultures (e.g. neutrophilic granulocytes, HL 60-cells, thrombocytes, etc.) Compound A was able to inhibit the cell death and "calcium overload" provoked by different agonists (e.g. PAF, leucotrienes, endothelin, FMLP or isoprenalin) as a function of the dosage ($IC_{50}$ values in the region of 1 μM).

The half-maximum inhibitory concentrations of test substances which inhibit the FMLP (1 nM)-induced calcium transients on $FLUO_3$-charged HL60 cells were measured.

| Compound No. | Half-maximum inhibitory concentration |
|---|---|
| 43 | $5 \cdot 10^{-5}$ M |
| 47 | $4,8 \cdot 10^{-5}$ M |
| 38a (Compound A) | $5,4 \cdot 10^{-6}$ M |

The test methods mentioned above are described by W. K. Pollock, T. J. Rink, R. F. Irvine, Biochem. J. 235:869–877 (1986) and by J. E. Merritt, R. Jacob, T. J. Hallam, J. of Biol. Chem. 264:1522–1527 (1989).

On individual HL-60 cells, the transmembranal influx through "unselective cation channels" after ATP stimulation was measured electrophysiologically by the patch clamp technique. This influx is inhibited by Compound A ($IC_{50}$:7 nM).

These findings are evidence of the direct point of attack on isolated cells. In particular, in the living organism, the granulocytes or leucocytes used in other tests migrate, after damage to brain cells (e.g. caused by stroke) into the damaged area, where they are activated by calcium-mediated processes, decompose and thereby release tissue-damaging mediators, including some chemotactic ones (e.g. PAF, leucotrienes, prostaglandins, FMLP etc.). Additional leucocytes attracted by chemotaxis increase the size of the damaged area. The test results described above show that this vicious circle can be stopped by the administration of the active substances described above. As a result the neurological damage is limited.

It has been demonstrated that conventional calcium antagonists (e.g. verapamil, nifedipine, diltiazem) do not inhibit the activation of leucocytes.

Further tests with Compound A support the above finding:

The direct neuronal attack of Compound A was demonstrated on isolated cortical and hippocampal neurone cells from foetal rat brains (prepared according to H. W. M üller and W. Seifert, Proc. Natl. Acad. Sci. USA 81:1248–1252, 1984; J. Neurosci. Res. 8:195–204, 1982; and Müller and Seifert in "Methods for Serum Free Culture of Neuronal and Lymphoid Cells," p. 67–77, A.R. Liss Inc., 150 Fifth Ave., New York, N.Y. 10011, 1984). In FURA$_2$-charged single cells the concentration-time curves (calcium transient) of the cytoplasmic Ca$^{2+}$ were recorded (method: modified from J. A. Condor, Proc. Natl. Acad. Sci. 83:6179–6183, 1986). Both after mechanical lesion and after the administration of excitatory amino acids (E.A.A., glutamate, cainate, quisqualate and NMDA) a sharp increase in the cytoplasmic calcium concentrations was induced, which could be inhibited by Compound A in every case as a function of dosage (IC$_{50}$ at 3 µM).

The mechanism of activity of this inhibition was investigated both on neuronal cell cultures and also on human neutrophilic granulocytes and HL 60 cells and thrombocytes. It has been shown that Compound A inhibits the transmembranal flow of calcium into the cells stimulated by receptor agonists (e.g. EAA, FMLP, leucotriene, PAF, endotheline etc.). This influx referred to by T. J. Hallam and T. J. Rink (Tips 10:8–10, 1989) as "receptor mediated Ca$^{2+}$ entry (RMCE)" cannot be inhibited by conventional calcium antagonists. Conventional calcium antagonists cannot prevent the leucocyte and thrombocyte activation since these cells do not have any voltage-dependent Ca$^{2+}$ channels. The blockade of the transmembranal calcium influx has been confirmed by electrophysiological means (voltage clamp technique) on HL60 cells and neurone cells.

The inhibition of blood clotting or blood platelet aggregation according to the invention can be demonstrated by standard tests: on QUIN 2-charged human blood platelets which have been stimulated with ADP, vasopressin, PGF2α, thrombin or serotonin, it can be demonstrated that the intracellular Ca-transient which results in platelet aggregation is inhibited by 3 µmol of Compound A.

In Patent Application EP-A-251 194 which has already been referred to, it is mentioned that in vitro tests on the smooth muscle (strips of aorta; C. van Breemen, P. Aarenson, R. Lautzenheiser, K. Meisheri, Chest 78:157S–165S (1980); R. Casteels and G. Droogman, J. Physio. 317:263–279 (1981) have shown that the compounds of formula I are calcium antagonists with a new mechanism of activity. It is emphasised, to make matters clear, that the tests referred to demonstrate the cardiovascular effect of the compounds. However, the test results obtained by them do not in any way make it obvious for the compounds of general formula I to have an effect on inflammatory or neuronal cells.

The compounds may be given orally, parenterally or topically. Suitable forms include, for example, tablets, capsules, suppositories, solutions, syrups, emulsions, aerosols or dispersible powders. Tablets may be produced, for example, by mixing the active substance or substances with known excipients, e.g. inert diluents such as calcium carbonate, calcium phosphate or lactose, disintegrants such as corn starch or alginic acid, binders such as starch or gelatine, lubricants such as magnesium stearate or talc and/or agents for obtaining delayed release, such as carboxypolymethylene, carboxymethylcellulose, cellulose acetate phthalate or polyvinylacetate. The tablets may also consist of several layers.

Coated tablets may be produced analogously by coating cores made in the same way as the tablets with substances conventionally used for tablet coatings, e.g. collidone or shellack, gum arabic, talc, titanium dioxide or sugar. In order to obtain delayed release or avoid incompatibilities, the core may also consist of several layers. Similarly, the tablet coating may consist of several layers to achieve delayed release, whilst the excipients mentioned for the tablets may be used.

Syrups containing the active substances or combinations of active substances according to the invention additionally contain a sweetener such as saccharin, cyclamate, glycerol or sugar as well as a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide or preservatives such as p-hydroxybenzoates.

Injectable solutions are produced in the usual way, e.g. by adding preservatives such as p-hydroxybenzoates or stabilisers such as alkali metal salts of ethylene diamine tetraacetic acid, and are then transferred into injection vials or ampoules.

Capsules containing one or more active substances or combinations of active substances may be prepared for example by mixing the active substances with inert carriers such as lactose or sorbitol and encapsulating them in gelatine capsules.

Suitable suppositories may be produced for example by mixing with carriers provided for this purpose, such as neutral fats or polyethyleneglycol or derivatives thereof.

The compounds may be administered according to the invention by enteral, parenteral or topical route, advantageously in a quantity of 0.05 to 500 mg per dose for adults. Preferably, 0.1 to 500 mg are used per dose for oral administration and 0.05 to 150 mg per dose for intravenous administration.

EXAMPLES OF FORMULATIONS

Example 1

Tablets

| | |
|---|---|
| Active substance according to invention | 40.0 mg |
| Lactose | 100.0 mg |
| Corn starch | 50.0 mg |
| Colloidal silica | 2.0 mg |
| Magnesium stearate | 3.0 mg |
| Total | 200.0 mg |

Method:

The active substance is mixed with some of the excipients and granulated with a solution of the soluble starch in water. After the granules have dried the remaining excipients are added and the mixture is compressed to form tablets.

Example 2

Coated tablets

| | |
|---|---|
| Active substance according to invention | 20.0 mg |
| Lactose | 100.0 mg |
| Corn starch | 65.0 mg |
| Colloidal silica | 2.0 mg |
| Soluble starch | 5.0 mg |
| Magnesium stearate | 3.0 mg |
| Total | 195.0 mg |

Method:

The active substance and excipients are compressed to form tablet cores as described in Example 1 and these are then coated with sugar, talc and gum arabic in the usual way.

Example 3

Suppositories

| | |
|---|---|
| Active substance according to invention | 50.0 mg |
| Lactose | 250.0 mg |
| suppository mass q.s. ad | 1.7 g |

Method:

The active substance and lactose are mixed together and the mixture is uniformly suspended in the molten suppository mass. The suspensions are poured into cooled moulds to form suppositories weighing 1.7 g.

Example 4

Ampoules

| | |
|---|---|
| Active substance according to the invention | 20.0 mg |
| Sodium chloride | 5.0 mg |
| Twice distilled water q.s. ad | 2.0 ml |

Method:

The active substance and sodium chloride are dissolved in twice distilled water and the solution is filtered into ampoules under sterile conditions.

Example 5

Ampoules

| | |
|---|---|
| Active substance according to invention | 10.0 mg |
| Sodium chloride | 7.0 mg |
| Twice distilled water q.s. ad | 1.0 mg |

Example 6

Drops

| | |
|---|---|
| Active substance according to invention | 0.70 g |
| Methyl p-hydroxybenzoate | 0.07 g |
| Propyl p-hydroxybenzoate | 0.03 g |
| Demineralised water q.s. ad | 100.00 ml |

Method:

The active substance and preservatives are dissolved in demineralised water, the solution is filtered and transferred into vials each holding 100 ml.

As has already been mentioned above, the compounds of formula Ie are new. They can be prepared analogously to the processes described in EP-A-00 37 934 and EP-A-251 194:

a) by cyclising a phenylmalonic acid diamide of formula III

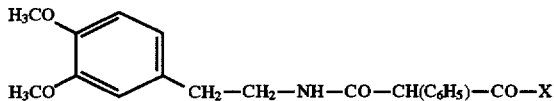

in the presence of a condensation agent or b) starting from carboxylic acids or carboxylic acid halides of formula IV wherein Y represents OH or halogen, by reacting with the amine of general formula VI

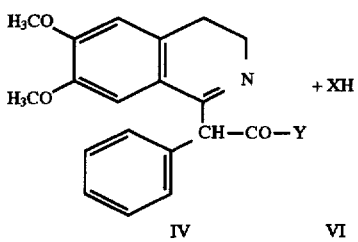

in the presence of a suitable condensation agent.

In the above formulae III and IV, is as defined for formula Ie. Suitable condensation agents for process a) according to the invention include numerous Lewis acids such as, e.g., phosphorus oxychloride, boron trifluoride, tin tetrachloride or titanium tetrachloride, as well as strong inorganic acids such as sulphuric, fluorosulphonic, hydrofluoric or polyphosphoric acid. They are generally used in an excess. Phosphorus oxychloride is preferred.

The reaction of cyclisation may be carried out in the presence or absence of a solvent. All inert solvents are suitable provided that they have sufficient solubility for the reactants and have a high enough boiling point. Examples include benzene, alkylbenzenes, chlorobenzenes, decalin, chloroform, methylene chloride, acetonitrile and the like. In a variant of the process the condensation agent, such as phosphorus oxychloride, is itself used as solvent.

No particular conditions apply to the reaction temperature. The reaction according to the invention can be carried out within a wide temperature range, preferably with warming or heating up to about the boiling point of the solvent.

The reaction of amidation b) can theoretically be carried out under the same conditions as reaction a). Examples of condensation agents additionally include carbodiimides such as cyclohexylcarbodiimide or carbonyldiimidazole.

Example 3,4-Dihydro-1-benzyl-6,7-dimethoxy-α-[di-2-(2,3,4-trimethoxyphenyl)ethyl]aminocarbonyl-isoquinoline hydrochloride

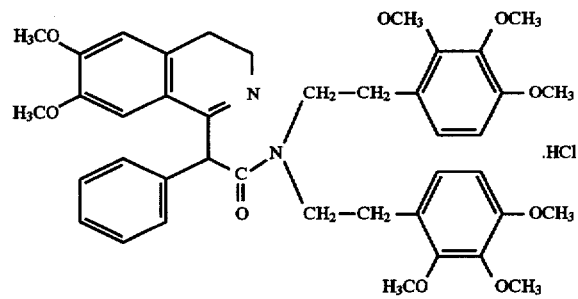

a) 2-(3,4-dimethoxyphenyl)ethylaminocarbonyl-phenylacetic acid-N,N-di-[2[(2,3,4-trimethoxyphenyl)-ethyl]amide At ambient temperature, 9.0 g (55.5 mmol) of N,N'-carbonyldiimidazole are stirred, in batches, into a solution of 18.0 g (52.4 mmol) of monoethyl-phenylmalonate-2-(3,4-dimethoxyphenyl)ethylamide in 150 ml of anhydrous dimethylformamide. After 30 minutes, 18.0 g (44.3 mmol) of di-[2-(2,3,4-trimethoxy-phenyl)ethylamine are added and the mixture is stirred for 30 minutes. The solvent is then distilled in vacuo, the residue is taken up in 1.5 litres of $CH_2Cl_2$ and extracted twice in succession with 250 ml of water and 200 ml of 1N HCl. The organic phase is dried over $Na_2SO_4$, concentrated by evaporation, and the residue is purified over a silica gel column (eluant: CH$_2$Cl$_2$/MeOH 100:2) and crystallised from ethyl acetate/ether. Yield:35.5 g b) 35.0 g (47.5 mmol) of amide (from Step a)) and 15 ml (164 mmol) of phosphorus oxychloride are heated to boiling for 30 minutes in 150 ml of anhydrous acetonitrile. After the reaction has ended (monitored by thin layer chromatography) the solvent and any unused phosphorus oxychloride are distilled off in vacuo. The residue is mixed with ice water, made alkaline with soda solution and extracted with about 1 liter of CH$_2$Cl$_2$ in batches. The organic phase is washed with water, dried over Na$_2$SO$_4$ and concentrated by evaporation. The residue is purified twice over a silica gel column (1st eluant: CH$_2$Cl$_2$:MeOH 100:2→100:4 ascending; 2nd eluant: CH$_2$Cl$_2$/ethyl acetate 1:1).

The hydrochloride is formed from the purified product (6.5 g) by dissolving in about 50 ml of ethanol and adding alcoholic hydrochloric acid. After evaporation and drying in a high vacuum at 50° C., 11.5 g of the desired product remain (Mp. 56°–64° C., amorphous)

Analogously to the Example, the Compounds of Table 12 can be prepared.

What is claimed is:

1. A method of providing cerebroprotection in a warm-blooded animal which comprises administering to said animal a therapeutically effective amount of a carbocyclically and heterocyclically fused dihydropyridine of formula

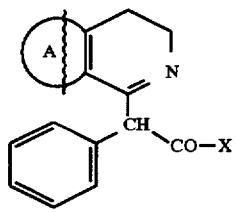

I or the tautomeric form thereof of formula

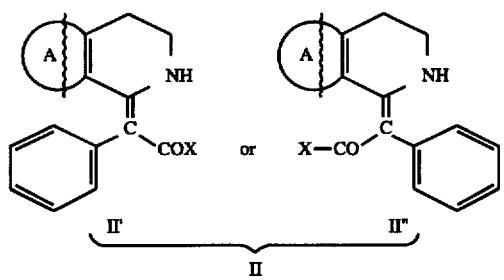

II wherein X represents OR$_1$; NHR$_2$; NR$_3$R$_4$ and

R$_1$ represents hydrogen, C$_{1-4}$-alkyl, C$_{1-4}$-alkoxyalkyl

R$_2$ represents hydrogen; C$_{3-6}$-alkenyl, C$_{3-6}$-alkynyl; C$_{3-6}$-cycloalkyl; C$_{3-6}$-cycloalkenyl; straight-chained or branched C$_{1-6}$-alkyl which may if desired be mono- or polysubstituted with the substituents of groups a) to c) listed below, which may be identical or different:

a) halogen; cyano; hydroxy; mercapto; C$_{1-4}$-alkoxy; C$_{1-4}$-alkylthio; amino; mono-C$_{1-4}$-alkylamino; di-C$_{1-4}$-alkylamino (wherein the alkyl radical may be identical or different) phenoxy (wherein the phenyl ring may be substituted as described in b) below.

b) phenyl; optionally mono- or polysubstituted, by identical or different substituents, by the groups halogen, trifluoromethyl, C$_{1-4}$-alkoxy, hydroxy, mercapto, C$_{1-4}$-alkylthio, C$_{1-4}$-alkyl, amino, mono-C$_{1-4}$-alkylamino, di-C$_{1-4}$-alkylamino (wherein the alkyl groups may be identical or different), C$_{2-3}$-acylamino, C$_{2-3}$-acyloxy and the group —O—(CH$_2$)$_n$—O vicinally by bound to the phenyl system (wherein n=1 or 2)

c) a 5- or 6-membered saturated or wholly or partially unsaturated monocyclic heterocyclic group having up to 3 heteroatoms selected from the group N, O, S; and as a bicyclic heterocycle indole (whilst the above-mentioned heterocycles may be mono- or polysubstituted by C$_{1-4}$-alkyl), C$_{3-6}$-cycloalkyl; C$_5$ or C$_6$-cycloalkenyl; C$_{2-3}$-acyl; C$_{1-4}$-alkylsulphonyl; or phenyl (which may in turn be substituted up to three times as described in b));

or R$_2$ represents phenyl, which may be substituted as described in b) above;

R$_3$ and R$_4$ independently of each other represent C$_{1-4}$-alkyl, which may if desired be phenyl-substituted, whilst the phenyl substituent may in turn be substituted as under b) hereinbefore; or R$_3$ and R$_4$ together with the nitrogen atom to which they are bound represent a wholly or partially saturated heterocyclic 5- or 6-membered ring (which may also contain up to 2 further heteroatoms from the group N, O, S), whilst the heterocyclic group thus obtained may be substituted by C$_{1-4}$-alkyl, hydroxy or (CH$_2$)$_p$-R$_5$ (where p=0 or 1) and R$_5$ represents a phenyl radical which is optionally substituted as under b) hereinbefore;

A represents the fused ring systems

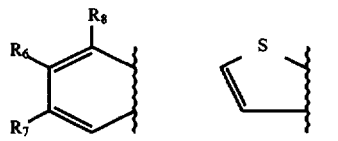

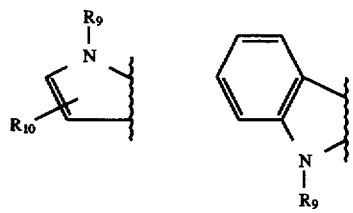

wherein

R$_8$ represents hydrogen; C$_{1-4}$-alkyl or C$_{1-4}$-alkoxy

R$_6$ and R$_7$ which may be identical or different represent hydrogen; hydroxy; C$_{1-4}$-alkyl; C$_{1-4}$-alkoxy; amino; methanesulphonylamino or R$_6$ and R$_7$ together represent -O—(CH$_2$)$_n$—O— (where n=1 or 2)

R$_9$ represents hydrogen; C$_{1-4}$-alkyl

R$_{10}$ represents hydrogen or 2-phenyl-2-ethoxycarbonylacetyl;

and the salts thereof with physiologically acceptable acids, bases or complex-forming agents.

2. The method as recited in claim 1 wherein the carbocyclically and heterocyclically fused dihydropyridine of formula I or II, wherein X represents OR$_1$ NHR$_2$; NR$_3$R$_4$ R$_1$ represents methyl or ethyl R$_2$ represents hydrogen; straight-chained or branched unsubstituted C$_{1-5}$-alkyl; allyl; propargyl; C$_{3-6}$- cycloalkyl; 3-chlorophenyl; 2-methyl-3-chlorophenyl; or $C_{1-3}$-alkyl, which is mono-substituted with one of the substituents of groups d) to f) listed hereinafter;

d) cyano, hydroxy, methoxy, dimethylamino e) phenyl, 3,4-methylenedioxyphenyl, mono-, di- or trimethoxy substituted phenyl, 3-methoxy-4-hydroxyphenyl, 3-hydroxy-4-methoxyphenyl, f) morpholino, pyridin-2-yl, indol-3-yl, furan-2-yl, thiphen-2-yl, pyridin-3-yl, pyridin-4-yl $R_3$ and $R_4$ independently of each other represent methyl; ethyl; 3-cyanopropyl; benzyl; or 3,4,5-trimethoxyphenethyl or $R_3$ and $R_4$ together with the nitrogen atom to which they are bound represent morpholine; thiomorpholine; pyrrolidine; piperazine; 4-methylpiperazine; 4-benzylpiperazine; or 4(2-methoxyphenyl)piperazine; and A represents the fused ring systems

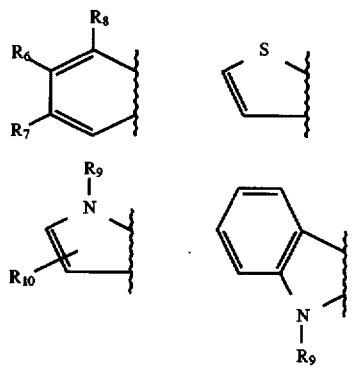

wherein $R_8$ represents hydrogen or methoxy $R_6$ represents methoxy; hydroxy; hydrogen; amino; or methanesulphonylamino $R_7$ represents hydrogen; methoxy; or hydroxy represents methyl $R_{10}$ represents 2-phenyl-2-ethoxycarbonylacetyl; or hydrogen.

3. The method as recited in claim 1 wherein the carboxycyclically and heterocyclically fused dihydropyridine of formula I or II, wherein A is the group

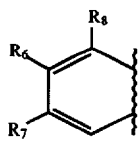

or

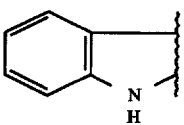

4. The method as recited in claim 1 to wherein the carboxycyclically and heterocyclically fused dihydropyridine of formula I or II, wherein $R_8$ is hydrogen and $R_6$ and $R_7$ independently of one another represent hydroxy or methoxy or together represent —O—$CH_2$—O—, $R_6$ and $R_7$ preferably representing methoxy.

5. The method as recited in claim 1 wherein the carboxycyclically and heterocyclically fused dihydropyridine formula I or II, wherein $R_6$ is —$NHR_2$ or —$NR_3R_4$.

6. The method as recited in claim 1 wherein the carboxycyclically and heterocyclically fused dihydropyridine of formula I or II, wherein X is $NHR_2$, and $R_2$ represents $C_{1-6}$-alkyl.

7. The method as recited in claim 1 wherein the carboxycyclically and heterocyclically fused dihydropyridine of formula I and II, wherein $R_2$ is $C_{1-6}$-alkyl which is unsubstituted or substituted by hydroxy, phenyl, (which may be substituted by hydroxy, methoxy or —O—$CH_2$—O—) or morpholino.

8. The method as recited in claim 1 wherein the carboxycyclically and heterocyclically fused dihydropyridine is of the formula

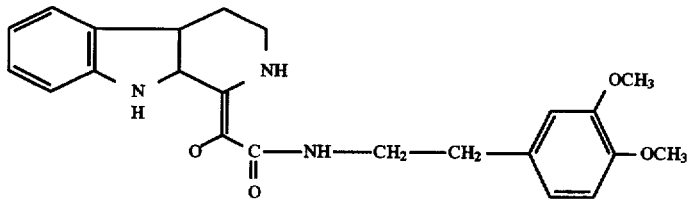

or a pharmaceutically acceptable salt thereof.

9. The method as recited in claim 1 wherein the carboxycyclically and heterocyclically fused dihydropyridine is of the formula

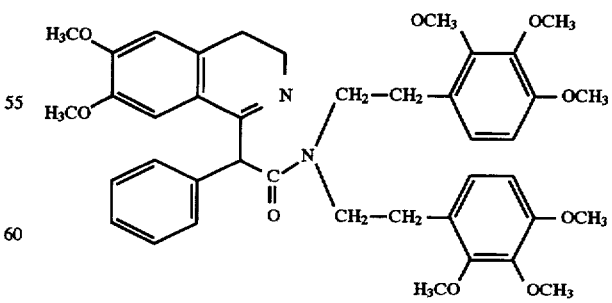

or a pharmaceutically acceptable salt thereof.

* * * * *